US010053519B2

(12) United States Patent
Goerlach-Doht et al.

(10) Patent No.: US 10,053,519 B2
(45) Date of Patent: *Aug. 21, 2018

(54) PROCESS FOR PRODUCING CELLULOSE DERIVATIVES OF HIGH BULK DENSITY, GOOD FLOWABILITY AND/OR DISPERSIBILITY IN COLD WATER AS WELL AS LOW SOLUTION COLOR

(71) Applicant: Dow Global Technologies LLC, Midland, MI (US)

(72) Inventors: Yvonne M. Goerlach-Doht, Rosengarten (DE); Juergen Hermanns, Nottensdorf (DE); Bettina Hoelzer, Walsrode (DE)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/096,704

(22) Filed: May 4, 2016

(65) Prior Publication Data

US 2016/0244533 A1 Aug. 25, 2016

Related U.S. Application Data

(62) Division of application No. 14/422,253, filed as application No. PCT/US2013/061109 on Sep. 23, 2013, now Pat. No. 9,340,624.

(Continued)

(51) Int. Cl.
*C08B 11/193* (2006.01)
*C08J 3/12* (2006.01)
(Continued)

(52) U.S. Cl.
CPC .......... *C08B 11/193* (2013.01); *A61K 9/4891* (2013.01); *A61K 47/38* (2013.01);
(Continued)

(58) Field of Classification Search
CPC ..... A61K 9/4891; A61K 47/38; C08B 11/193
See application file for complete search history.

(56) References Cited

U.S. PATENT DOCUMENTS

| 2,331,864 A | 10/1943 | Swinehart et al. |
| 4,091,205 A | 5/1978 | Onda et al. |

(Continued)

FOREIGN PATENT DOCUMENTS

| EP | 210917 | 2/1987 |
| EP | 0714656 A1 | 6/1996 |

(Continued)

OTHER PUBLICATIONS

Comparison of Laser Diffraction and Image Analysis, Partec 2007, Kohler et al.

(Continued)

*Primary Examiner* — Melvin C. Mayes
*Assistant Examiner* — Stefanie J Cohen

(57) ABSTRACT

A particulate cellulose derivative is obtained in a process of grinding and drying a moist cellulose derivative which comprises the steps of A) providing a cellulose derivative having a moisture content of from 60 to 95 percent, based on the total weight of the moist cellulose derivative, B) grinding and partially drying the moist cellulose derivative in a gas-swept impact mill;

C) contacting the ground and partially dried cellulose derivative with an additional amount of a drying gas outside the gas-swept impact mill; and D) subjecting the cellulose derivative to partial depolymerization after having contacted the cellulose derivative with a drying gas in step C).

(Continued)

The obtained particulate cellulose derivative has a high untapped bulk density, a good flowability and a low color intensity.

12 Claims, 1 Drawing Sheet

Related U.S. Application Data

(60) Provisional application No. 61/705,200, filed on Sep. 25, 2012.

(51) Int. Cl.
*C08L 1/08* (2006.01)
*C08L 1/26* (2006.01)
*C08L 1/28* (2006.01)
*C09D 101/08* (2006.01)
*C09D 101/26* (2006.01)
*A61K 9/48* (2006.01)
*A61K 47/38* (2006.01)

(52) U.S. Cl.
CPC ............... *C08J 3/124* (2013.01); *C08L 1/08* (2013.01); *C08L 1/26* (2013.01); *C08L 1/28* (2013.01); *C08L 1/284* (2013.01); *C09D 101/08* (2013.01); *C09D 101/26* (2013.01); *C08J 2301/08* (2013.01); *Y10T 428/2982* (2015.01)

(56) References Cited

U.S. PATENT DOCUMENTS

| | | |
|---|---|---|
| 4,316,982 A | 2/1982 | Holst et al. |
| 4,979,681 A | 12/1990 | Donges et al. |
| 6,410,050 B1 | 6/2002 | Yang |
| 7,361,753 B2 | 4/2008 | Hammes et al. |
| 2001/0025101 A1 | 9/2001 | Schlesiger et al. |
| 2001/0034441 A1 | 10/2001 | Schlesiger et al. |
| 2003/0122003 A1 | 7/2003 | Schlesiger et al. |
| 2006/0155013 A1 | 7/2006 | Bumm et al. |
| 2007/0175361 A1 | 8/2007 | Bonney et al. |
| 2008/0039621 A1 | 2/2008 | Maruyama et al. |
| 2008/0207893 A1 | 8/2008 | Berglund et al. |
| 2010/0063269 A1 | 3/2010 | Mallon |

FOREIGN PATENT DOCUMENTS

| | | | |
|---|---|---|---|
| EP | 0824107 A2 | 2/1998 | |
| EP | 1099709 A1 | 5/2001 | |
| GB | 804306 | 11/1958 | |
| GB | 2262527 | 6/1993 | |
| WO | 9600748 A1 | 1/1996 | |
| WO | 9831710 | 7/1998 | |
| WO | 0032637 A1 | 6/2000 | |
| WO | 2003018637 | 3/2003 | |
| WO | 2008050209 A1 | 5/2008 | |
| WO | 2008067930 A1 | 6/2008 | |
| WO | 2012015400 A1 | 2/2012 | |
| WO | 2012138533 A1 | 10/2012 | |
| WO | WO2012138532 | * 10/2012 | ............ A61K 9/146 |

OTHER PUBLICATIONS

Viscometry—Determination of kinematic viscosity using the Ubbelohde viscometer—Apparatus and measurement procedure; DIN 51562-1, 1999 Ed., Jan. 1, 1999; Deutsches Institut fur Normung E.V. (DIN).

Standard Test Method for Color of Clear Liquids (Platinum-Cobalt Scale)1; ASTM D1209-05, 2011.

* cited by examiner

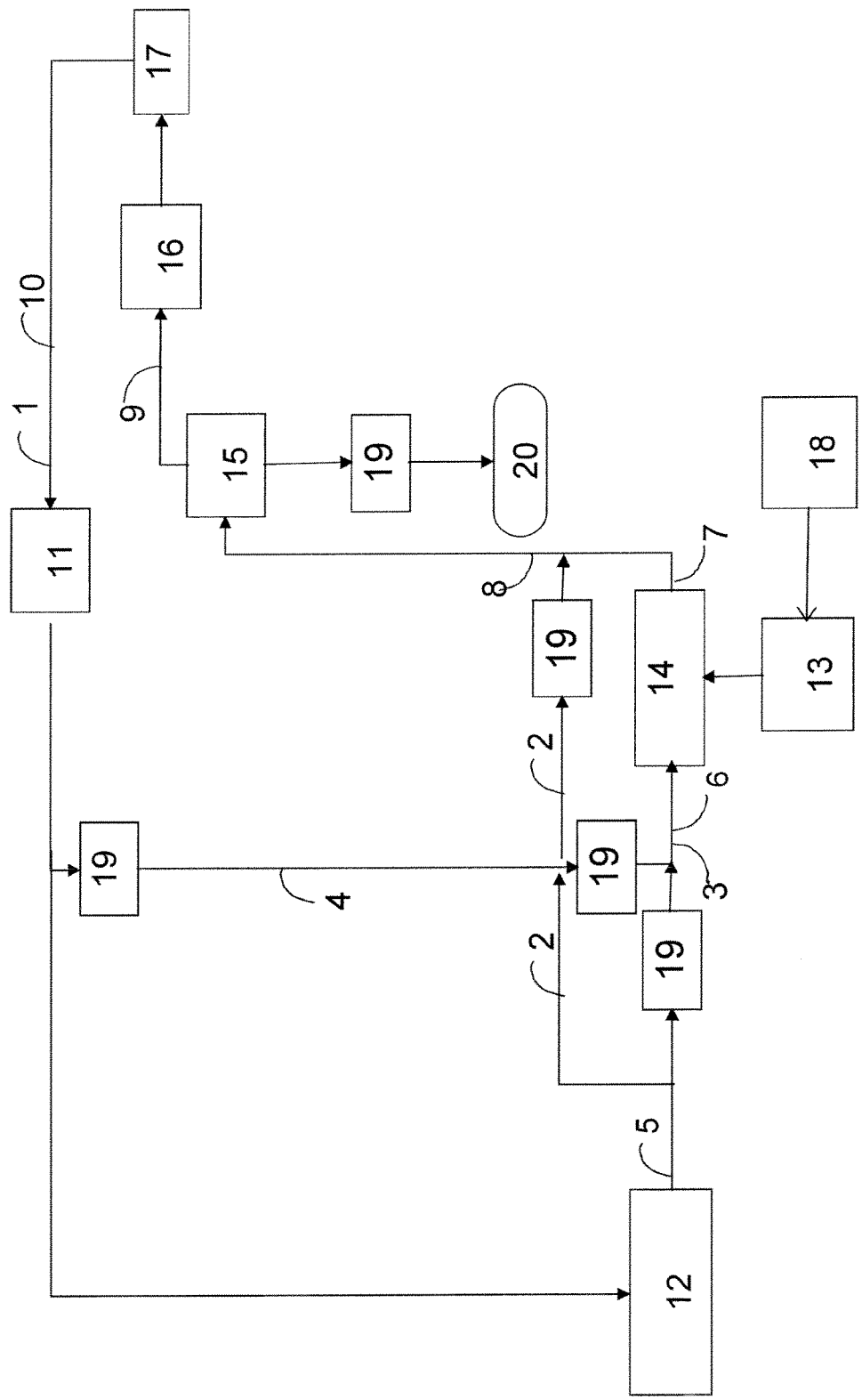

PROCESS FOR PRODUCING CELLULOSE DERIVATIVES OF HIGH BULK DENSITY, GOOD FLOWABILITY AND/OR DISPERSIBILITY IN COLD WATER AS WELL AS LOW SOLUTION COLOR

This application is a DIV of application Ser. No. 14/422253, filed Feb. 18, 2015, now U.S. Pat. No. 9,340,624, which is a national stage of International Application No. PCT/US2013/061109, filed Sep. 23, 2013, which claims priority of U.S. PRO Application No. 61/705200, filed Sep. 25, 2012. The disclosure of all applications cited in this paragraph are incorporated herein in their entirety by reference.

FIELD

The present invention relates to a particulate cellulose derivative of high bulk density, good flowability and/or dispersibility in cold water as well as low solution color and to a process for producing such particulate cellulose derivative.

INTRODUCTION

Cellulose derivatives are industrially important and are used in a large variety of technology areas and in many different end-use applications, for example in the personal care or pharmaceutical industry, in agricultural applications, and in the building or oil industry. Their preparation, properties and applications are described, for example, in Ullmann's Encyclopedia of Industrial Chemistry, 5th Edition, (1986), Volume A5, pages 461-488, VCH Verlagsgesellschaft, Weinheim or in "Methoden der organischen Chemie" (methods of organic chemistry), 4th Edition (1987), Volume E20, Makromolekulare Stoffe, Part Volume 3, pages 2048-2076, Georg Thieme Verlag, Stuttgart.

Water-soluble cellulose derivatives have found widespread use. These water-soluble cellulose derivatives are conveniently supplied as a particulate dry material that is then dissolved in water for the desired end use of such water-soluble cellulose derivatives.

It is desirable that the cellulose derivatives have a reasonably high bulk density and a good flowability to facilitate transportation and handling of the cellulose derivatives.

Unfortunately, many water-soluble cellulose derivatives are not dispersible in cold water. Non-dispersibility is due to the large surface area and fibrous nature of the cellulose derivatives. The large surface area leads to the outside particles of the cellulose derivatives being hydrated before the inside of the particles when added to water. A gelatinous membrane of hydrated outside particles is thus formed around the inside particles, shielding the inside particles from complete hydration. The first particles that come into contact with water immediately swell and stick to each other, forming a gel-like barrier that shields the remaining particles from hydration. This gel-blocking behavior of water-soluble cellulose derivatives is a considerable drawback for those applications that comprise the solution of the particulate water-soluble cellulose derivatives such as cellulose ethers in aqueous systems. The gel blocking behavior is visible as the formation of "lumps" which require a long time for complete dissolution. To overcome this gel blocking behavior or the formation of lumps the cellulose derivatives are dispersed in hot water, typically above about 80° C. During agitation the dispersion is cooled and dissolution of the cellulose derivative takes place. At a specific temperature the cellulose derivative starts to dissolve and to build up viscosity. This so-called hot/cold water dissolution technique takes advantage of the fact that water-soluble cellulose derivatives such as cellulose ethers are generally insoluble in hot water and soluble in cold water, depending on the type and degree of substitution. Unfortunately, this hot/cold water dissolution technique is quite time-consuming for those who have to prepare aqueous solutions of the cellulose derivatives. Accordingly, the skilled artisans have intensely searched for ways of making cellulose derivatives dispersible in cold water, i.e., water below, at or only slightly above room temperature, without the formation of a substantial amount of lumps. Various methods have been suggested, such as temporarily cross-linking with a dialdehyde such as glyoxal or treatment with surfactants. However, these methods are not desirable for cellulose ethers in pharmaceutical or food applications. Other methods describe the usage of tensides (surfactants) added to the cellulose during production, see U.S. Pat. No. 7,361,753 B2, or surface coating using additives such as a salts, sugars, surfactants or low molecular weight water soluble polymers during the drying process, see US Patent Application Publication No. 2007/0175361.

British Patent Specification GB 804,306 discloses a process wherein a wet mixture comprising from 2 to 35 percent of fibrous cold-water soluble cellulose ether and from 98 to 65 percent by weight of hot water is formed at a temperature above the gel point of the cellulose ether, the mixture is cooled below its gel point, e.g. to 20° C., until the fibrous structure substantially disappears and the mass becomes transparent, the temperature is raised to a point above which syneresis occurs, e.g. to 90° C., then the mixture is maintained at a point above the gel point until dry, e.g. in an oven, and the dried product is reduced to the desired particle size, e.g. such that 92% or more of the cellulose ether pass through a 42 mesh screen (corresponding to an opening of 354 micrometers). However, such process has been too time and energy intense to be used on large scale.

U.S. Pat. No. 2,331,864 discloses a method of treating a fibrous cold-water soluble cellulose ether to improve its rate of solution in cold water. In the disclosed process the water content of the water-wet fibrous cellulose ether is set to a value of from 72 to 88 percent by weight at a temperature above 50° C., preferably above 70° C., by making a uniform slurry of from 1 to 5 weight percent of methylcellulose in hot water and subsequent removal of the excess water, e.g., by pressing or by filtering under vacuum. The moist mass is cooled to a temperature below 50° C., preferably to 5-23° C. The cooled mass is allowed to age until the desired degree of gel formation has taken place, i.e., until the mass becomes translucent and substantially without visible fibrous structure. Then the mass is immediately dried at a temperature above 50° C. by spreading it on trays and blowing a stream of hot air over it to a moisture content of less than 15 percent. The dried product is ground. Product of 60 to 100 mesh fineness or finer is obtained and is said to be a free-flowing, non-caking powder which dissolves readily when simply stirred with cold water. However, the disclosed process involves many steps and is time-consuming. Moreover, the wet mass of 72-88 percent water content appears to be sticky and hard to homogeneously handle as described in U.S. Pat. No. 2,331,864 on a large scale. Plugging issues during the described partial drying on trays will lead to inoperability in a manufacturing process because big lump formation will block the transport of the material.

The International Patent Application WO 96/00748 discloses a process for the extrusion of an aqueous hydrated cellulose ether having a water content of 40-75% and a temperature below 40° C. through a plurality of orifices of cross-sectional area of 0.0075-1 mm² to form an elongated cellulose ether extrudate in the shape of strands, drying and then cutting the elongated cellulose ether extrudate to the desired length. After having dried the cellulose ether to a moisture content of about 25 percent, cutting can be conducted in an air-swept impact mill wherein hot air is blown across the mill Cellulose ether particles of good dispersibility in water are achieved, but unfortunately the process is not used on large scale due to the high equipment costs when extruding the aqueous hydrated cellulose ether into strands and subsequently cutting them in an air-swept impact mill.

One aspect of the present invention is to provide cellulose derivatives which have a good flowability in combination with a reasonably high untapped bulk density.

A preferred object of the present invention is to provide cellulose derivatives which have a good flowability in combination with a reasonably high untapped bulk density and which are also well dispersible in cold water.

Another preferred object of the present invention is to provide a process for producing such cellulose derivatives which does not require the time-consuming steps like drying in an oven or on trays and subsequent grinding as disclosed in British Patent Specification GB 804,306 and in U.S. Pat. No. 2,331,864.

Yet another preferred object of the present invention is to provide a process for producing such cellulose derivatives which does not require extruding the cellulose derivatives to strands and cutting the strands as disclosed in WO 96/00748.

Surprisingly, it has been found that the flowability and/or the cold water dispersibility of cellulose derivatives in particulate form can be improved in a novel process for grinding and drying a moist cellulose derivative. Several processes for combined drying and grinding of moist cellulose derivatives are known in the art, such as described in the patent applications GB 2 262 527 A; EP 0 824 107 A2; EP-B 0 370 447 (equivalent to U.S. Pat. No. 4,979,681); EP 1 127 895 A1 (equivalent to US 2001/034441) and EP 0 954 536 A1 (equivalent to U.S. Pat. No. 6,320,043), but none of these references addresses the problem of improving the cold water dispersibility of cellulose derivatives or provide an evidence of good flowability of the cellulose derivatives.

Co-pending patent application PCT/US12/031112, filed 29 Mar. 2012, discloses a process wherein a cellulose derivative that has a moisture content of from 25 to 95 percent, based on the total weight of the moist cellulose derivative, is ground and partially dried in a gas-swept impact mill wherein the gas fed into the impact mill has a temperature of 100° C. or less; and the ground and partially dried cellulose derivative is contacted with an additional amount of a drying gas outside the gas-swept impact mill that has a higher temperature than the gas fed into the impact mill. Some of the inventors who contributed to the co-pending patent application PCT/US12/031112 also contributed to this patent application.

Cellulose derivatives that are used for the manufacture of capsules or for coating dosage forms like tablets usually are partially depolymerized, which is apparent by their low viscosity as aqueous solutions. Cellulose derivatives having a viscosity of from 2.4 to 200 mPa·s, measured as a 2 weight-% solution in water at 20° C., are commonly used for the manufacture of capsules or for coating dosage forms.

The co-pending patent application PCT/US12/031112 illustrates the utility of the process disclosed therein for drying and grinding a partially depolymerized cellulose derivative for obtaining a cellulose derivative of high bulk density, good flowability and/or good dispersibility in cold water. In addition to high bulk density, good flowability and/or good dispersibility in cold water, it is highly desirable that cellulose derivatives that are used for the manufacture of capsules or for coating dosage forms have a low color in solution for providing clear coatings or capsules of light color. Unfortunately, the drying and grinding of the partially depolymerized cellulose derivative increases the color intensity of the cellulose derivative in solution due to impact and heat during drying and grinding.

The inventors of the present patent application have surprisingly found a way of modifying the process disclosed in the co-pending patent application PCT/US12/031112 in such a manner that dried and ground cellulose derivatives of i) high bulk density, ii) low solution color, and iii) good flowability and/or good dispersibility in cold water are obtained.

SUMMARY

One aspect of the present invention is a process for producing a particulate cellulose derivative, which comprises the steps of A) providing a cellulose derivative having a moisture content of from 25 to 95 percent, based on the total weight of the moist cellulose derivative, B) grinding and partially drying the moist cellulose derivative in a gas-swept impact mill wherein the gas fed into the impact mill has a temperature of 100° C. or less; C) contacting the ground and partially dried cellulose derivative with an additional amount of a drying gas outside the gas-swept impact mill, wherein the additional amount of drying gas outside the gas-swept impact mill has a higher temperature than the gas fed into the impact mill; and D) subjecting the cellulose derivative to partial depolymerization after having contacted the cellulose derivative with a drying gas in step C).

Another aspect of the present invention is a particulate cellulose derivative producible by the above-mentioned process.

Yet another aspect of the present invention is a method of improving the flowability and/or the cold water dispersibility of a particulate cellulose derivative, which method comprises the steps of A) providing a cellulose derivative having a moisture content of from 25 to 95 percent, based on the total weight of the moist cellulose derivative, B) grinding and partially drying the moist cellulose derivative in a gas-swept impact mill wherein the gas fed into the impact mill has a temperature of 100° C. or less; C) contacting the ground and partially dried cellulose derivative with an additional amount of a drying gas outside the gas-swept impact mill, wherein the additional amount of drying gas outside the gas-swept impact mill has a higher temperature than the gas fed into the impact mill, and D) subjecting the cellulose derivative to partial depolymerization after having contacted the cellulose derivative with a drying gas in step C).

Yet another aspect of the present invention is a particulate cellulose derivative having an untapped bulk density of at least 370 g/l, a Carr Index of 20 or less, a viscosity of from 1.2 to 200 mPa·s, measured as a 2 weight-% solution in water at 20° C. according to DIN 51562-1:1999-01; and a color of not more than 40 APHA color units, determined as a 2 weight-% solution in water at 20° C. according to ASTM D1209-05 (2011).

Yet another aspect of the present invention is an aqueous composition produced by blending water, the above-mentioned particulate cellulose derivative and one or more optional additives.

Yet another aspect of the present invention is a process for the manufacture of capsules which comprises the step of contacting the above-mentioned aqueous composition with dipping pins.

Yet another aspect of the present invention is a process for coating a dosage form which comprises the step of contacting the above-mentioned aqueous composition with the dosage form.

It has been surprisingly been found that a cellulose derivative of lower color intensity in solution is obtained if the cellulose derivative is subjected to partial depolymerization after drying and grinding steps A) to C) as described above than if the partial depolymerization is conducted prior to the drying and grinding steps A) to C).

BRIEF DESCRIPTION OF DRAWINGS

FIG. 1 illustrates a flow sheet of the drying and grinding steps A) to C) of the process of the present invention.

DETAILED DESCRIPTION

The present invention relates to a process for producing a particulate cellulose derivative by drying and grinding a moist cellulose derivative.

The cellulose derivatives used in this process are generally soluble or at least soakable in solvents, preferably water. They can have one or more substituents, preferably of the types: hydroxyethyl, hydroxypropyl, hydroxybutyl, methyl, ethyl, propyl, dihydroxypropyl, carboxymethyl, sulfoethyl, hydrophobic long-chain branched and unbranched alkyl groups, hydrophobic long-chain branched and unbranched alkyl aryl groups or aryl alkyl groups, cationic groups, acetate, propionate, butyrate, lactate, nitrate or sulfate, of which some groups, such as, for example, hydroxyethyl, hydroxypropyl, hydroxybutyl, dihydroxypropyl and lactate, are capable of forming grafts. The substituents of the celluloses according to the invention are not limited to these groups.

Preferred cellulose derivatives are cellulose esters or cellulose ethers. Useful cellulose ethers are, for example, carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses.

The cellulose ether preferably is an alkyl cellulose, hydroxyalkyl cellulose or hydroxyalkyl alkylcellulose. This means that in the cellulose ether of the present invention, at least a part of the hydroxyl groups of the anhydroglucose units are substituted by alkoxyl groups or hydroxyalkoxyl groups or a combination of alkoxyl and hydroxyalkoxyl groups. Typically one or two kinds of hydroxyalkoxyl groups are present in the cellulose ether. Preferably a single kind of hydroxyalkoxyl group, more preferably hydroxypropoxyl, is present.

Particularly preferred cellulose ethers are those having a thermal flocculation point in water, such as, for example, methylcellulose, hydroxypropyl methylcellulose, hydroxyethyl methylcellulose, ethylhydroxy ethylcellulose, and hydroxypropyl cellulose. The cellulose ethers are preferably water-soluble, i.e., they have a solubility in water of at least 1 gram, more preferably at least 2 grams, and most preferably at least 5 grams in 100 grams of distilled water at 25° C. and 1 atmosphere.

Preferred alkyl hydroxyalkyl celluloses including mixed alkyl hydroxyalkyl celluloses are hydroxyalkyl methylcelluloses, such as hydroxyethyl methylcelluloses, hydroxypropyl methylcelluloses or hydroxybutyl methylcelluloses; or hydroxyalkyl ethyl celluloses, such as hydroxypropyl ethylcelluloses, ethyl hydroxyethyl celluloses, ethyl hydroxypropyl celluloses or ethyl hydroxybutyl celluloses; or ethyl hydroxypropyl methylcelluloses, ethyl hydroxyethyl methylcelluloses, hydroxyethyl hydroxypropyl methylcelluloses or alkoxy hydroxyethyl hydroxypropyl celluloses, the alkoxy group being straight-chain or branched and containing 2 to 8 carbon atoms. Preferred hydroxyalkyl celluloses are hydroxyethyl celluloses, hydroxypropyl celluloses or hydroxybutyl celluloses; or mixed hydroxylkyl celluloses, such as hydroxyethyl hydroxypropyl celluloses.

Preferred are hydroxyalkyl alkylcelluloses, more preferred are hydroxyalkyl methylcelluloses and most preferred are hydroxypropyl methylcelluloses, which have an MS (hydroxyalkoxyl) and a DS (alkoxyl) described below. The degree of the substitution of hydroxyl groups of the anhydroglucose units by hydroxyalkoxyl groups is expressed by the molar substitution of hydroxyalkoxyl groups, the MS (hydroxyalkoxyl). The MS (hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylation agent, e.g. a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone. The term "hydroxyalkoxyl groups" thus has to be interpreted in the context of the MS (hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS (hydroxyalkoxyl).

The hydroxyalkyl alkylcelluloses generally has a molar substitution of hydroxyalkoxyl groups in the range of 0.05 to 1.00, preferably 0.08 to 0.90, more preferably 0.12 to 0.70, most preferably 0.15 to 0.60, and particularly 0.20 to 0.50. The average number of hydroxyl groups substituted by alkoxyl groups, such as methoxyl groups, per anhydroglucose unit, is designated as the degree of substitution of alkoxyl groups, DS (alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The hydroxyalkyl alkylcelluloses according to this invention preferably have a DS (alkoxyl) in the range of 1.0 to 2.5, more preferably 1.1 to 2.4, most preferably 1.2 to 2.2 and particularly 1.6 to 2.05. Most preferably the cellulose ether is a hydroxypropyl methylcellulose or hydroxyethyl methylcellulose having a DS (methoxyl) within the ranges indicated above for DS (alkoxyl) and an MS (hydroxypropoxyl) or an MS (hydroxyethoxyl) within the ranges indicated above for MS (hydroxyalkoxyl). The degree of substitution of alkoxyl groups and the molar substitution of hydroxyalkoxyl groups can be determined by Zeisel cleavage of the cellulose ether with hydrogen iodide and subsequent quantitative gas chromatographic analysis (G. Bartelmus and R. Ketterer, Z. Anal. Chem., 286 (1977) 161-190).

Preferred alkyl celluloses are methylcelluloses. The average number of hydroxyl groups substituted by methoxyl groups per anhydroglucose unit is designated as the degree of substitution of methoxyl groups (DS). The methylcellulose preferably has a DS of from 1.20 to 2.25, more preferably from 1.25 to 2.20, and most preferably from 1.40 to 2.10. The determination of the % methoxyl in methylcellulose is carried out according to the United States Pharmacopeia (USP 34). The values obtained are % methoxyl. These are subsequently converted into degree of substitution (DS) for methoxyl substituents.

The viscosity of the cellulose derivative used in the process of the present invention is generally more than 200 mPa·s, preferably from 500 to 200,000 mPa·s, more preferably from 500 to 100,000 mPa·s, most preferably from 1000 to 80,000, and particularly from 1000 to 60,000, measured as a 2 weight-% solution in water at 20° C., measured according to DIN 51562-1:1999-01.

The production of cellulose derivatives, preferably cellulose ethers and cellulose esters, is known in the art. Typically the production process involves activating the cellulose, for example by treatment with an alkali metal hydroxide, reacting the thus treated cellulose with a derivatizing agent, such as an etherifying or esterifying agent, and washing the cellulose derivative to remove by-products. After the washing step the cellulose derivative generally has a moisture content of from 25 to 60 percent, typically from 40 to 55 percent, based on the total weight of the moist cellulose derivative. While the preferred washing liquor may depend on the specific type of cellulose derivative, preferred washing liquors generally are water, isopropanol, acetone, methylethylketone or brine. More preferred washing liquors generally are water or brine. Cellulose derivatives are generally washed at a temperature of from 20 to 120° C., preferably from 65 to 95° C. A solvent-moist, preferably a water-moist filter cake is obtained after washing and separating the cellulose derivative from the washing liquor. The moist cellulose derivative is usually obtained in the shape of moist granules, moist lumps and/or a moist paste.

According to one aspect of the present invention the cellulose derivative has been obtained by separating a cellulose derivative from a suspension thereof in a liquid, such as water, and is subsequently subjected to the process of the present invention. The suspension of particles in a liquid can originate from the production and washing the cellulose derivative, as described above. Separating a cellulose derivative from a suspension can be carried out in a known way, such as centrifugation.

According to another aspect of the present invention a dry cellulose derivative and a liquid, such as water, can be mixed in a compounder to a desired moisture content and the thus obtained moist cellulose derivative is subsequently subjected to the process of the present invention.

It is a great advantage of the process of the present invention that cold water dispersible cellulose derivatives can be obtained without mixing a substantial amount of a surface-treatment additive with the cellulose derivative and a liquid, such as water. Therefore, according to a preferred embodiment of the present invention no substantial amount of a surface-treatment additive is added to the cellulose derivative. By "no substantial amount of a surface-treatment additive" is meant an amount that does not significantly change the surface properties and in particular the cold water dispersibility of the cellulose derivative. Preferably not more than 1 percent, more preferably not more than 0.5 percent, most preferably not more than 0.2 percent, and particularly no amount of a surface-treatment additive is added to the cellulose derivative, based on the dry weight of the cellulose derivative. Surface-treatment additives are, for example, surfactants, such as sorbitol or lauryl sulfates; esters; salts, such as KCl, phosphates, nitrates or sulfates; or sugars, such as lactose, fructose, glucose, sucrose, or maltodextrin; or low molecular weight polymers, such as polyethylene glycols, or propylene glycols. The compounder preferably allows thorough and intense mixing. Useful compounders are, for example, granulators, kneaders, extruders, presses, or roller mills, wherein the mixture of the cellulose derivative and liquid is homogenised by applying shear forces and compounding, such as a twin-screw compounder. Co-rotating as well as counter-rotating machines are suitable. So-called divided trough kneaders with two horizontally arranged agitator blades that engage deeply with one another and that perform a mutual stripping action, as in the case of twin-screw compounders are particularly suitable. Suitable single-shaft, continuous kneaders include the so-called Reflector® compounders, which are high performance mixers of modular construction, consisting of a multi-part, heatable and coolable mixing cylinder and a unilaterally mounted blade mixer (manufacturer: Lipp, Germany) Also suitable are so-called pinned cylinder extruders or Stiftconvert® extruders (manufacturer: Berstorff, Germany) The pins incorporated in the housing serve as abutments in order to prevent the kneaded material rotating together with the shaft. Kneader mixers with so-called double-blade sigma stirrers (manufacturer: Fima, Germany) in a horizontal assembly are particularly suitable. The blades operate at different speeds and their direction of rotation can be reversed. A stirred vessel with a vertically arranged mixer shaft is also suitable if suitable flow baffles are mounted on the vessel wall in order to prevent the kneaded mass rotating together with the stirrer shaft, and in this way an intensive mixing action is imparted to the kneaded material (manufacturer: Bayer AG). Also suitable are double-walled mixing vessels with a planetary stirrer and inline homogeniser.

In step A) of the process and method of the present invention a cellulose derivative is provided that has a moisture content of from 25 to 95 percent, based on the total weight of the moist polysaccharide derivative. Preferred lower limits of the moisture content are 30, 35 and 38 percent respectively. Preferred upper limits of the moisture content are 80, 70 and 60 percent respectively. Most preferably the moisture content is from 40 to 50 percent. The moisture content can be adjusted by addition of a liquid, for example, water, isopropanol, acetone, methylethylketone or brine. Most preferably, water is used. The amount of liquid added to the water-soluble cellulose derivative should be adjusted to the moisture content that the cellulose derivative already has. The moisture content can be determined by ASTM method D-2363-79 (reapproved 1989). The moist cellulose derivative in step A) preferably does not comprise a substantial amount of a surface-treatment additive that is left on the cellulose derivative upon drying of the cellulose derivative, such as the above-mentioned surface-treatment additives. Preferably the cellulose derivative does not comprise more than 1 percent, more preferably not more than 0.5 percent, most preferably not more than 0.2 percent, based on the dry weight of the cellulose derivative, and particularly no amount of a surface-treatment additive. It is to be understood that any residual amounts of by-products from the production of the cellulose derivative, such as sodium hydrochloride, is not encompassed by the term "surface-treatment additive".

The temperature of the cellulose derivative prior to drying and grinding is preferably controlled and optionally varied or adjusted in a range from 5 to 60° C., more preferably from 5 to 45° C., most preferably from 10 to 40° C., and particularly from 10 to 30° C. If a liquid such as water is added to the cellulose derivative prior to drying and grinding, the temperature of the cellulose derivative prior to drying and grinding is preferably controlled and optionally varied or adjusted by controlling and optionally varying or adjusting the temperature of the added liquid and/or the jacket temperature of the compounder.

The cellulose derivative having a moisture content of from 25 to 95 percent is usually in the shape of moist granules, moist lumps and/or a moist paste. In step B) it is subjected to grinding and partially drying in a gas-swept impact mill, preferably an air-swept impact mill, wherein the cellulose derivative is subjected to an impacting and/or shearing stress. Preferred gas-swept impact mills are Ultra Rotor mills (Altenburger Maschinen Jaeckering, Germany) or Turbofiner PLM mills (PALLMANN Maschinenfabrik GmbH & Co. KG, Germany) Gas classifier mills are also useful gas-swept impact mills, for example, the Hosokawa Alpine Air Classifier mill—ZPS Circoplex Hosokawa Micron Ltd., Cheshire, England. Drying is typically accomplished with a combination of gas and mechanical energy. Air or nitrogen gas can be used. In the process of the present invention the gas fed into the impact mill has a temperature of 100° C. or less, preferably of 75° C. or less, more preferably of 50° C. or less. Typically the gas fed into the impact mill has a temperature of 10° C. or more, preferably of 20° C. or more, more preferably of 30° C. or more. A gas stream having the above-mentioned temperature can be created in various ways. In one embodiment of the invention a fresh gas stream having the desired temperature can be fed into the impact mill. In another embodiment of the invention a recycled gas stream having the desired temperature is fed into the impact mill. For example, a gas stream can be separated from the ground and dried cellulose derivative obtained in step C) as described further below, and the resulting solid-free gas stream, or a portion thereof, can be cooled in a cooling system, e.g., using water as coolant. This resulting cooled gas stream can be fed into the mill. Alternatively, the entire amount of cooled gas can be re-heated, e.g. in a natural gas burner. To bring the re-heated gas to the desired temperature for feeding into the impact mill, a separate stream of cold gas can be combined with the hot gas stream before feeding the gas stream into the mill. The gas and the wet product stream are generally fed via separate inlets into the mill, typically gas from the bottom and wet product at a side entrance via a feed screw system connected to the mill. In one aspect of step B) of the process the moist cellulose derivative and a gas are fed into the gas-swept impact mill at a rate of 10 to 90 m$^3$/kg, more preferably of 20 to 50 m$^3$/kg cellulose derivative, based on the dry weight of cellulose derivative. The circumferential speed of the gas-swept impact mill is preferably not more than 100 m/s. More preferably, the gas-swept impact mill is operated in such a manner that its circumferential speed is in a range from 30 to 100 m/s, most preferably from 35 to 80 m/s.

It is an essential feature of the process of the present invention that in step B) of the process the moist cellulose derivative is ground but only partially dried and in step C) of the process the ground and partially dried cellulose derivative is contacted with an additional amount of a drying gas outside the gas-swept impact mill. Preferably the ratio of the gas flow in the gas-swept impact mill in step B) and the flow of the additional amount of drying gas in step C), i.e. (gas flow in step B)/(additional gas flow in step C) is from 1:10 to 8:1, preferably from 1:5 to 3:1, more preferably from 1:3 to 2:1, most preferably from 1:2 to 1:1, and particularly from 1:1.5 to 1:1. The term "additional amount of a drying gas" as used herein means a drying gas that has not been fed into the gas-swept impact mill. The skilled artisan knows how to achieve only a partial drying in step B). E.g., the gas stream can be determined that would be necessary to essentially dry the cellulose derivative in the gas-swept impact mill at the given process parameters, such as gas temperature and moisture content and temperature of the moist cellulose derivative. Incomplete drying can be achieved in step B), e.g., by feeding a lower amount of gas per unit of cellulose derivative to be ground and dried into the gas-swept impact mill than the amount of gas that would be required to dry and grind the cellulose derivative to an essentially dry product in the gas-swept impact mill. In a preferred aspect of the present invention the gas stream used for drying the cellulose derivative is split into two streams via a slide valve wherein the first gas stream is fed into the gas-swept impact mill and the second gas stream is contacted with the ground and partially dried cellulose derivative that leaves the impact mill. Furthermore, it has been found that a particulate cellulose derivate of improved flowability and/or cold water dispersibility can be obtained if the additional amount of drying gas utilized in step C) outside the gas-swept impact mill (i.e., the second gas stream), has a higher temperature than the gas fed into the impact mill (i e, the first gas stream). Preferably, the additional amount of drying gas outside the gas-swept impact mill has a temperature that is at least 70° C. higher, more preferably from 100 to 220° C. higher, most preferably from 100 to 180° C. higher than the gas fed into the impact mill. The temperature of the additional amount of drying gas outside the gas-swept impact mill preferably is from 80 to 340° C., more preferably from 100 to 220° C., and most preferably from 125 to 210° C. The flow of the drying gas outside the gas-swept impact mill is preferably chosen to result in a rate of 20 to 100 m$^3$/kg, more preferably from 25 to 80 m$^3$/kg, based on the dry weight of cellulose derivative in the gas-swept mill.

The first gas stream leaving the impact mill can have a higher or lower temperature than the gas stream fed into the impact mill. The temperature of the first gas stream leaving the impact mill depends on various factors, such as the temperature, amount and moisture content of the moist cellulose derivative and the mechanical energy in the impact mill. The first gas stream leaving the impact mill can be partially or fully separated from the ground and partially dried cellulose derivative before the cellulose derivative is contacted with the second gas stream, but preferably the cellulose derivative is suspended in at least a portion or, more preferably, in the entire amount of the gas stream exiting the gas-swept impact mill when it is contacted with the second gas stream. The amount and the temperature of the second gas stream, i.e. the additional amount of drying gas outside the gas-swept impact mill, is preferably chosen such that the combined gas stream in step C), which is a combination of the first gas stream leaving the impact mill and the additional amount of drying gas utilized in step C), has a temperature which is at least 30° C. higher, more preferably from 35 to 100° C. higher, and most preferably from 40 to 90° C. higher than the temperature of the first gas stream leaving the impact mill.

In the drying step C) of the process of the present invention the moisture content of the cellulose derivative is typically reduced to 1 to 20 percent, preferably 2 to 10 percent, more preferably 3 to 8 percent, based on the total weight of the moist cellulose derivative.

After step C) the ground and dried cellulose derivative particles are preferably separated from the flow of gas in a separator arranged down-stream the gas-swept impact mill. The separator is preferably designed to conduct gas classification, such as air classification. It can be a centrifugal separator such as, for example, a cyclone, or a filtering separator such as a sifter. Alternatively, depending on the construction of the gas-swept impact mill, a gas classification may already take place in the gas-swept impact mill. The flow of gas that has been separated from the cellulose derivative particles can be recycled and re-used in steps B) and/or C) of the process of the present invention. Alternatively, the flow of gas that has been separated from the cellulose derivative particles is not recycled and not re-used in steps B) and C) of the process of the present invention, but fresh gas from the environment is used in steps B) and/or C).

The cellulose derivative obtained after steps A) to C) of the process of the present invention has an increased bulk density, as compared to a cellulose derivative that has not been treated by steps A) to C). The increased bulk density enables a higher load of the reactor which is used for the subsequent partial depolymerization step D). After having contacted the cellulose derivative with a drying gas in step C), the viscosity of the cellulose derivative is generally more than 200 mPa·s, preferably from 500 to 200,000 mPa·s, more preferably from 500 to 100,000 mPa·s, most preferably from 1000 to 80,000, and particularly from 1000 to 60,000, measured as a 2 weight-% solution in water at 20° C. according to DIN 51562-1:1999-01.

In an optional sieving step between the drying step C) and the partial depolymerization step D) of the process of the present invention the ground and dried cellulose derivative can be sieved through a sieve of from 125 to 400, preferably from 160 to 355, more preferably from 180 to 315, and most preferably from 200 to 300 micrometers mesh size, for example a sieve of 220 μm mesh size. The optional sieving step can be conducted after having separated the ground and dried cellulose derivative from the flow of gas in a separator arranged down-stream the gas-swept impact mill, such as a cyclone. Useful sieves are known in the art and described in DIN 4188. A fine fraction having a particle size below the mesh size of the sieve and a coarse fraction having a particle size above the mesh size of the sieve is obtained. These two fractions can be used separately as final products according to the invention, showing cold water dispersibility for both the fine fraction as well as for the coarse fraction. Alternatively, in the process of the present invention the ground and dried cellulose derivative is not sieved through a sieve. According to the process of the present invention cold water dispersible cellulose derivatives are producible regardless whether the ground and dried cellulose derivative is sieved or not. The entire amount of ground and dried cellulose derivative is water dispersible. This is a great advantage since the entire amount of ground and dried cellulose derivative is useful and no amount needs to be recycled to the drying and grinding process or used for other purposes where cold water dispersibility is of less importance.

The cellulose derivative is subjected to partial depolymerization in a further step D). Preferably the partial depolymerization of the cellulose derivative is conducted in such a manner to achieve a reduction in viscosity of the cellulose derivative of at least 10 percent, preferably at least 20 percent, and more preferably at least 50 percent, based on the viscosity prior to partial depolymerization. After partial depolymerization the viscosity of the cellulose derivative is from generally from 1.2 to 200 mPa·s, preferably from 2 to 100 mPa·s, more preferably from 2.5 to 50 mPa·s, and in particular from 3 to 30 mPa·s, measured as a 2 weight-% solution in water at 20° C. according to DIN 51562-1:1999-01. Partial depolymerization processes are generally known in the art.

The cellulose derivative can be contacted with an acid, preferably a strong acid, to conduct partial depolymerization. The amount of the acid is generally in the range from 0.1 to 5 percent by weight, based on the weight of the starting cellulose derivative. Preferred acids are hydrogen halides, such as hydrogen chloride. The acid can be in gaseous form, for example as described in European Patent Application EP 1,141,029, or in the form of an aqueous solution, for example as described in European Patent Application EP 210,917. When the acid is used in the form of an aqueous solution, the amount of the water is generally in the range from 3 to 8 percent by weight, based on the weight of the cellulose derivative used as a starting material. The partial depolymerization is generally conducted at a temperature in the range of from 50 to 130° C., preferably from 60 to 110° C., more preferably from 65 to 90° C.

Alternatively, the cellulose derivative can be contacted with an oxidizing agent to conduct partial depolymerization. Exemplary of suitable oxidizing agents are ozone, peroxides, halites, halates, perhalates, hypohalites and perborates, and hydrogen peroxide. Preferred oxidizing agents are alkali metal chlorites, alkali metal chlorates, such as potassium chlorate or sodium chlorate, alkali metal perchlorates, alkali metal periodates, alkali metal hypobromites, alkali metal hypochlorites, alkali metal hypoiodites, alkali metal peroxides, and hydrogen peroxide. Sodium and potassium are the preferred alkali metals. The amount of the oxidizing agent is generally in the range from 0.01 to 3 percent by weight, based on the starting cellulose derivative. The usage of an oxidizing agent is described in U.S. Pat. No. 4,316,982 and the prior art discussed therein.

The acid and the oxidizing agent can be used separately or in combination. A combined usage is described in European Patent Application EP 1,423,433. The above described process is useful for improving the flowability and/or cold water dispersibility of particulate cellulose derivatives.

The particulate cellulose derivative that is produced according to the process of the present invention generally has an untapped bulk density of at least 370 g/l, preferably at least 400 g/l, and more preferably even at least 430 g/l. Untapped bulk densities of up to 530 g/l are generally achieved, or under optimized conditions even up to 600 g/l. Bulk density (BD) as used herein is defined as the ratio of apparent volume to mass of the material taken, called untapped bulk density, and also the ratio of tapped volume to mass of material taken, called tapped bulk density. A useful procedure for measuring these bulk densities is described in United States Pharmacopeia 24, Test 616 "Bulk Density and Tapped Density," United States Pharmacopeia Convention, Inc., Rockville, Md., 1999.

The particulate cellulose derivative that is produced according to the process of the present invention generally has a Carr index of 20 or less, preferably of 18 or less, more preferably of 16 or less, and under optimized conditions of less than 15. The minimum Carr index is 1. The Carr index of the particulate cellulose derivative typically is 5 or more, more typically 8 or more. The Carr index C is an indication of the compressibility of a powder. It is calculated by the formula $$C=100*(BD\ tapped-BD\ untapped)/BD\ tapped,$$

wherein "BD tapped" is the tapped bulk density of a powder and "BD untapped" is the untapped bulk density of a powder. The Carr index is frequently used in the pharmaceutical science as an indication of the flowability of a powder. A Carr index below 15 is considered to be an indication of good flowability. (Kanig, Joseph L.; Lachman, Leon; Lieberman, Herbert A. (1986). *The Theory and Practice of Industrial Pharmacy* (3 ed.). Philadelphia: Lea & Febiger.)

The particulate cellulose derivative that is produced according to the process of the present invention has a good dispersibility in cold water. By "cold water" is meant water below, at or only slightly above room temperature, i.e., water at a temperature of generally 0 to 40° C., typically 5 to 30° C., more typically 10 to 25° C. The dispersibility in cold water is determined as described in the examples. A criterion for poor or no cold water dispersibility is visible by lump formation of the cellulose derivative in cold water. The lump formation strongly hinders the dissolution of the product over time.

Moreover, the process of the present invention is useful for producing cellulose derivatives of a certain size and shape. Particle size and shape of a particulate cellulose derivative can be determined by a high speed image analysis method which combines particle size and shape analysis of sample images. An image analysis method for complex powders is described in: W. Witt, U. Köhler, J. List, Current Limits of Particle Size and Shape Analysis with High Speed Image Analysis, PARTEC 2007. A high speed image analysis system is commercially available from Sympatec GmbH, Clausthal-Zellerfeld, Germany as dynamic image analysis (DIA) system QICPIC™. The high speed image analysis system is useful for measuring among others the following dimensional parameters of particles:

EQPC: EQPC of a particle is defined as the diameter of a circle that has the same area as the projection area of the particle. For the purpose of the present invention the median EQPC is the volume distribution average of all particles in a given sample of a particulate cellulose derivative, designated as EQPC 50,3. The volume distribution is designated by the number 3 after the comma. The median EQPC means that 50% of the EQPC of the particle distribution is smaller than the given value in μm and 50% is larger.

LEFI: The particle length LEFI is defined as the longest direct path that connects the ends of the particle within the contour of the particle. "Direct" means without loops or branches. For the purpose of the present invention the median LEFI is the volume distribution average of all particles in a given sample of a particulate cellulose derivative, designated as LEFI 50,3. The volume distribution is designated by the number 3 after the comma. The median LEFI means that 50% of the LEFI of the particle distribution is smaller than the given value in μm and 50% is larger.

The particulate cellulose derivative that is produced according to the process of the present invention generally has a median Equivalent Projected Circle Diameter (EQPC) of at least 50 micrometers, preferably at least 70 micrometers, and in some preferred embodiments of the invention at least 100 micrometers. The particulate cellulose derivative generally has a median EQPC of up to 500 micrometers, preferably up to 400 micrometers, more preferably up to 300 micrometers, and most preferably up to 200 micrometers.

The particulate cellulose derivative that is produced according to the process of the present invention generally has a median LEFI of from 50 to 600 micrometers, preferably from 80 to 500 micrometers, and most preferably from 100 to 400 micrometers.

Furthermore, by the process of the present invention, wherein a cellulose derivative is subjected to a partial depolymerization step D) after drying and grinding steps A) to C) as described above, a cellulose derivative of lower color intensity in solution is obtained than in a comparable process wherein the partial depolymerization is conducted prior to the drying and grinding steps A) to C). The particulate cellulose derivative that is produced according to the process of the present invention generally has a color of not more than 40 APHA color units, preferably not more than 38 APHA color units, and most preferably not more than 35 APHA color units, determined as a 2 weight-% solution in water at 20° C. according to ASTM D1209-05 (2011). The particulate cellulose derivative that is produced according to the process of the present invention generally has a color of 20 APHA color units or more, typically of 25 APHA color units or more, determined as a 2 weight-% solution in water at 20° C. For preparing the 2 weight-% solution of the cellulose derivative in water at 20° C. the procedure described United States Pharmacopeia (USP 35, "Hypromellose", pages 3467-3469 is applied.

A preferred embodiment of carrying out steps A) to C) of the process of the present invention is illustrated by FIG. 1 which is described in more detail below, but which is not to be construed to limit the scope of the present invention to the embodiment of the invention illustrated by FIG. 1.

Description of Fig. 1
1 Total gas stream
2 Gas stream through bypass
3 Gas stream through gas swept impact mill
4 Cooled gas stream
5 Heated gas stream after burner
6 Temperature of gas stream before gas swept impact mill
7 Temperature of gas stream after gas swept impact mill, ° C.
8 Combined gas stream
9 gas stream before filter
10 Temperature gas stream before blower, ° C.
11 Blower
12 Burner
13 Mill feed unit
14 Gas swept impact mill
15 Cyclone
16 Filter
17 Washer/Cooler
18 Moisturized Cellulose Derivative
19 Valve
20 Product As used herein, the terms "after the burner", "after the blower" etc. relate to the direction of the gas stream and have the meaning of "downstream the burner" and downstream the blower etc. A blower 11 circulates air or preferably nitrogen through a mill circuit, providing a total gas stream 1 of preferably 1000-2200 m³/h measured by a flow meter. After the blower 11 the total gas stream 1 can be split into a cooled gas stream 4 and a gas stream through a burner 12. This heated gas stream 5 after the burner can be split into a gas stream 3 through a gas swept impact mill 14 and into a gas stream 2 through a bypass, which serves as an additional amount of a drying gas outside the gas-swept impact mill. In one embodiment of the invention the entire amount of the heated gas stream 5 after the burner is fed as a gas stream 2 through a bypass; this means that only the cooled gas stream 4 is fed into the gas swept impact mill 14 and the amount of the cooled gas stream 4 corresponds to the amount of the gas stream 3 that flows through gas swept impact mill. The examples of the present invention make use of this embodiment. The moisturized cellulose derivative 18 can be added through a mill feed unit 13, comprising a feed screw system into the gas swept impact mill 14. The temperature 6 of the gas stream 3 before the gas swept impact mill is measured. The temperature of the gas stream 7 after the gas swept impact mill is measured as well. After the junction of the gas stream 2 through the bypass and the gas stream 3 through the gas swept impact mill, the temperature of the combined gas stream 8 containing the ground cellulose derivative is measured. The conduit after the mill till the beginning of a cyclone 15 can be considered as flash dryer. The combined gas stream 8 is fed to the cyclone 15 where substantially the entire amount of cellulose derivative, except some residual amount of fine particles (dust) is separated from the gas stream. The residual amount of dust is removed in a filter 16. The temperature of the gas stream 9 before the filter 16 is measured after it has left the cyclone 15 and before it enters the filter 16. The filtered gas stream is passed through a washer/cooler 17. The temperature 10 of the washed and cooled gas stream is measured; the washed and cooled gas stream corresponds to the total gas stream 1 that is circulated by the blower 11. The flow of the gas streams as described above is controlled by means of valves 19. The design of each of these valves is not necessarily the same but adjusted to the temperature and volume of the gas streams. The product 20 is fed to a reactor suitable for carrying out the partial depolymerization step D) (not shown).

The present invention further relates to particulate cellulose derivatives having i) an untapped bulk density of at least 370 g/l, preferably at least 400 g/l, and more preferably at least 430 g/l, ii) a Carr Index of 20 or less, preferably of 18 or less, more preferably of 16 or less, and in some embodiments of the invention a Carr index of even less than 15, iii) a viscosity of from 1.2 to 200 mPa·s, preferably from 2.0 to 100 mPa·s, more preferably from 2.5 to 50 mPa·s, and in particular from 3 to 30 mPa·s, measured as a 2 weight-% solution in water at 20° C. according to DIN 51562-1:1999-01, and iv) a color of not more than 40 APHA color units, preferably not more than 38 APHA color units, and more preferably not more than 35 APHA color units, determined as a 2 weight-% solution in water at 20° C. according to ASTM D1209-05 (2011). The particulate cellulose derivatives of the present invention typically have an untapped bulk density of up to 600 g/l, more typically of up to 550 g/l, and most typically up to 510 g/l.

The Carr index of the particulate cellulose derivative typically is 8 or more, more typically 10 or more, and most typically 12 or more. The particulate cellulose derivative generally has a color of 20 APHA color units or more, typically of 25 APHA color units or more.

The particulate cellulose derivative of the present invention generally has a median Equivalent Projected Circle Diameter (EQPC) of at least 50 micrometers, preferably at least 70 micrometers, and in some preferred embodiments of the invention at least 100 micrometers. The particulate cellulose derivative generally has a median EQPC of up to 500 micrometers, preferably up to 400 micrometers, more preferably up to 300 micrometers, and most preferably up to 200 micrometers. The particulate cellulose derivative of the present invention generally has a median LEFI of from 50 to 600 micrometers, preferably from 80 to 500 micrometers, and most preferably from 100 to 400 micrometers.

The particulate cellulose derivative that is produced according to the process of the present invention and the novel particulate cellulose derivative of the present invention are useful in a variety of applications, where good dispersibility of the particulate cellulose derivative in cold water is beneficial. For example, the particulate cellulose derivative is useful in pharmaceutical applications, preferably in liquid suspensions comprising a cellulose derivative and a medicament, or in aqueous solutions of the particulate cellulose derivative for the preparation of hard shell capsules.

Another aspect of the present invention is an aqueous composition which has been produced by blending water, the particulate cellulose derivative of the present invention and one or more optional additives. Preferably water, the particulate cellulose derivative of the present invention and one or more optional additives are blended in such an amount such that the composition preferably comprises from 5 to 40 percent, more preferably from 10 to 30 percent, of the cellulose derivative of the present invention, based on the total weight of the aqueous composition. This aqueous composition is particularly useful for the manufacture of capsules or coatings of dosage forms. Optional additives may be incorporated in the composition, such as coloring agents, flavor and taste improvers, antioxidants, plasticizers, and surfactants. For example, when producing capsules a water-soluble food dye, such as red oxide, or a natural dye, may be used as a coloring agent; $TiO_2$ may be used as a masking agent; polyethylene glycol, polypropylene glycol, sorbitol or glycerin may be used as a plasticizer or as a surfactant to improve the flexibility of the capsule film. Particularly useful additives for coatings of solid forms are single layer film plasticizers, solids-loading enhancers, a second cellulose derivative, preferably a second cellulose ether, surfactants, lubricants, polishing agents, pigments, anti-tack agents, glidants, opacifiers, coloring agents and any combination thereof.

In one aspect of the present invention, the aqueous composition may be used for coating dosage forms, such as tablets, granules, pellets, caplets, lozenges, suppositories, pessaries or implantable dosage forms, to form a coated composition. Preferred dosage forms are pharmaceutical dosage forms, nutrition supplements or agricultural dosage forms.

In another aspect of the present invention the aqueous composition may be used for the manufacture of capsules. One method for the manufacture of capsules is the "hot-pin method". This method preferably comprises the steps of (a) providing the above-mentioned aqueous composition, (b) pre-heating dipping pins so that they are at a temperature above the gelation temperature of the aqueous composition when dipped into the aqueous composition, (c) dipping the pre-heated dipping pins into the aqueous composition maintained at a temperature below its gelation temperature, (d) withdrawing the dipping pins from the aqueous composition obtaining a film on the dipping pins, and (e) drying the film on the dipping pins at a temperature above the gelation temperature of the aqueous composition so as to obtain molded capsule shells on the pins. The hot-pin method used to prepare capsules from the aqueous composition of the cellulose ether is described in detail in the International Patent Publication No. WO 2008/050209.

Another method for the manufacture of capsules is the "cold-pin method". In this method the above-mentioned aqueous composition additionally comprises a gelling agent such as carrageenan, pectin, gellan gum, or another sequestering agent or gelling aid, such as potassium, magnesium, ammonium, or calcium ions. In the cold-pin method pins are generally kept at room temperature and are dipped into the aqueous composition maintained at a temperature above its gelation temperature, preferably at a temperature of 45 to 60° C., the dipping pins are withdrawn from the aqueous composition and a film is obtained on the dipping pins, and the film is dried on the dipping pins to obtain molded capsule shells on the pins. The cold-pin method used to prepare capsules from the above-mentioned aqueous composition is described in detail in European Patent Application No. EP 0 714 656 and in U.S. Pat. No. 6,410,050.

EXAMPLES

Unless otherwise mentioned, all parts and percentages are by weight. In the Examples the following test procedures are used.

The determination of the % methoxyl and % hydroxypropoxyl in hydroxypropyl methylcellulose (HPMC) was carried out according to the United States Pharmacopeia (USP 35, "Hypromellose", pages 3467-3469). The values obtained are % methoxyl and % hydroxypropoxyl. These can be subsequently converted into degree of substitution (DS) for methyl substituents and molar substitution (MS) for hydroxypropyl substituents. Residual amounts of salt are taken into account in the conversion.

The viscosity of the HPMC samples was measured as a 2.0% by weight solution in water at 20° C. The 2.0% by weight HPMC solution in water was prepared according to United States Pharmacopeia (USP 35, "Hypromellose", pages 3467-3469) followed by an Ubbelohde viscosity measurement according to DIN 51562-1:1999-01 (January 1999).

The tapped and untapped bulk density of the HPMC in particulate form was measured using a Hosokawa Powder Characteristics Tester: Model PT-N available from Hosokawa Micron, Osaka Japan.

The Carr index C is calculated by the formula
C=100*(BD tapped−BD untapped)/BD tapped, wherein "BD tapped" is the tapped bulk density of a powder and "BD untapped" is the untapped bulk density of a powder.

The median LEFI and the median EQPC are the volume distribution average of the LEFIs and EQPCs of all particles in a given sample of a particulate cellulose derivative. The median LEFI and the median EQPC, designated as LEFI 50,3 and EQPC 50,3 in Table 1 below, were measured by an image analyzer (high speed image analyzer sensor QICPIC, Sympatec, Germany, with dry disperser RODOS/L with an inner diameter of 4 mm and dry feeder VIBRI/L and Software WINDOXS, Vers. 5.3.0 and M7 lens).

The dispersibility in cold water (CWD) and torque build-up reflecting viscosity build-up of the particulate cellulose derivatives after 60 minutes were determined according to the following procedure: A jacketed glass vessel of 250 ml was filled with 125 ml of tap water of 20° C. The jacket of the vessel was kept at 20° C. by a thermostat. A torque measurement agitator device (Haake VT 550, Thermo Scientific, Karlsruhe, Germany) carrying an agitator being equipped with two rectangular blades, each one perforated with a 8 mm hole, was used for the measurement. The agitator blades were mounted on opposite sides with a 10 degree pitch against the axis, fully covered with the liquid in the vessel, having a distance from the vessel wall of 5 mm. The agitator was turned on to 250 rpm. 10% by weight of cellulose ether were dosed in one batch into the vessel containing the water while agitating constantly. A criterion for poor cold water dispersibility was visible by lump formation of the cellulose ether in cold water causing irregular torque peaks. The lump formation strongly hinders the dissolution of the cellulose derivative over time.

The APHA color units were determined as a 2 weight-% solution in water at 20° C.

The 2.0% by weight HPMC solution in water was prepared according to United States Pharmacopeia (USP 35, "Hypromellose", pages 3467-3469) followed by a measurement of the APHA color units according to ASTM D1209-05 (2011).

Examples 1-5

Drying-Grinding Steps A)-C)

A commercially available continuous compounder with heating and cooling jacket was used to add water to dry a cellulose derivative. The cellulose derivative used as a starting material in Examples 1-5 was hydroxypropyl methylcellulose (HPMC) having a moisture content of 1%, a median Equivalent Projected Circle Diameter (EQPC 50,3) of 81 µm, a median particle length (LEFI 50,3) of 249 µm, an untapped bulk density (BD) of 294 g/l, a tapped bulk density (BD) of 438 g/l and a Carr Index of 33. The HPMC had 29.3% methoxyl groups, 6.2% hydroxypropoxyl groups and a viscosity of 5200 mPa·s, measured as a 2.0% by weight solution in water at 20° C. The HPMC used as a starting material was not soluble in cold water, which was visible as lumps in the above described method for determining the dispersibility in cold water (CWD).

The compounder jacket was supplied with a fluid which was used to adapt the temperature of the HPMC prior to drying and grinding, as listed in Table 1 below. The HPMC was fed continuously at a feed rate as listed in Table 1 below into the compounder. Water of a temperature of about 5° C. was continuously added to the compounder. The moisturized cellulose derivative 18 (HPCM in the present examples) was transported continuously via a transport belt into a mill feed unit 13 (Altenburger Maschinen Jaeckering GmbH, Hamm, Germany) The mill feed unit was a vessel equipped with a vessel agitator having blades and a single auger screw. The bottom blades of the vessel agitator pressed the moist HPMC paste into a single auger screw mounted at the bottom of the vessel. The moist HPMC was forced through a perforated plate directly into the side of a gas swept impact mill 14 (an Ultrarotor II "S" impact mill from Altenburger Maschinen Jaeckering GmbH, Hamm, Germany, between the first and second grinding stage). The gas swept impact mill was equipped with seven grinding stages. The bottom five grinding stages were equipped with standard grinding bars. No grinding bars were installed in the top two grinding stages. The interior of the mill jacket had the standard Altenburger corrugated stationary grinding plates.

The rotor of the impact mill was operated at a circumferential speed as listed in Table 1 below. A specific gas flow system used herein was a closed loop system applying nitrogen as gas. The gas flow system was composed of three separately controllable gas streams. The control operation was carried out by slide valves allowing controlling the amount of the respective gas stream. At the same time the temperature of the gas streams could be controlled via a natural gas burner and a gas cooling system using cold water as coolant. The resulting gas temperatures of the respective gas streams are listed in Table 1 below. The flow of the gas streams applied in Examples 1-5 is listed in Table 1 below and is illustrated in FIG. 1.

The conditions of steps A) to C) of the process of the present invention and the properties of the produced particulate HPMC's prepared in steps A) to C) of are listed in Table 1 below.

TABLE 1

| No. in FIG. 1 | Example | 1 | 2 | 3 | 4 | 5 |
|---|---|---|---|---|---|---|
| 18 | HPMC Moisture before grinding [%] | 73 | 73 | 74 | 75 | 73 |
|  | HPMC Temperature before grinding [° C.] | 19 | 39 | 20 | 40 | 21 |
|  | Water Temperature [° C.] | 6 | 6 | 5 | 5 | 5 |
| 1 | Total Gas stream [m³/h] | 1100 | 1050 | 1150 | 1150 | 1100 |
| 2 | Gas stream through bypass [m³/h] | 650 | 600 | 650 | 650 | 600 |
| 3 | Gas stream through mill [m³/h] | 450 | 450 | 500 | 500 | 500 |
| 4 | Cooled gas flow [m³/h] | 450 | 450 | 500 | 500 | 500 |
|  | Throughput HPMC, based on dry weight [kg/h] | 16 | 19 | 19 | 18 | 20 |
|  | Gas through mill/HPMC in Mill [m³/kg] | 28 | 24 | 26 | 28 | 25 |
|  | Gas through bypass/HPMC in Mill [m³/kg] | 41 | 32 | 34 | 36 | 30 |
|  | Circumferential Speed of mill [m/s] | 69 | 69 | 86 | 86 | 78 |
| 2, 5 | Temp. of heated gas stream after burner and in by-pass [° C.] | 196 | 202 | 133 | 131 | 185 |
| 6 | Temperature of gas stream before mill [° C.] | 26 | 25 | 28 | 25 | 29 |
|  | Difference between temperature in by-pass 2 and in gas stream 6 before mill | 170 | 177 | 105 | 106 | 156 |
| 7 | Temperature gas stream after mill [° C.] | 48 | 48 | 51 | 51 | 49 |
| 8 | Temperature of combined gas stream [° C.] | 136 | 136 | 100 | 97 | 128 |
|  | Difference between temp. in gas stream 7 after mill and in combined gas stream 8 | 88 | 88 | 49 | 46 | 79 |
| 9 | Temperature gas stream before filter [° C.] | 117 | 117 | 90 | 88 | 109 |
| 10 | Temperature gas stream before blower [° C.] | 21 | 22 | 30 | 25 | 26 |
|  | Difference between gas temperature in bypass and gas temperature after mill [° C.] | 170 | 177 | 106 | 106 | 156 |
|  | Final Moisture [%] | 6.8 | 6.8 | 4.0 | 6.1 | 5.4 |
|  | EQPC 50,3 [µm] | 261 | 256 | 188 | 175 | 225 |
|  | LEFI 50,3 [µm] | 400 | 380 | 304 | 280 | 360 |
|  | BD untapped [g/l] | 435 | 436 | 505 | 509 | 456 |
|  | BD tapped [g/l] | 508 | 513 | 599 | 594 | 536 |
|  | Carr Index | 14 | 15 | 16 | 14 | 15 |
|  | Cold Water Dispersible (yes/no) | Yes | yes | yes | yes | yes |

No lump formation could be detected for Examples 1-5. The cellulose derivatives were fully dissolved already after 30 minutes, showing a constant torque and viscosity.

Examples 1-5

Partial Depolymerization Step D)

Samples of the HPMC produced in steps A)-C) of Examples 1-5 as described above were partially depolymerized by heating the powderous samples with gaseous hydrogen chloride at a time and temperature listed in Table 2 below.
40 kg of the HPMC were loaded into a jacketed blender (1000 L capacity). After purging with nitrogen gas heating was started and continued until a constant jacket outlet temperature of 85° C. was reached. Then 72 g of dry hydrogen chloride gas were added in 1 min at 6 full rotations of the jacketed blender per minute. The reaction time as listed was conducted at 85° C. jacket outlet temperature and 6 full rotations of the jacketed blender per min. Then the HCl gas was removed via evacuation, the heating was stopped and the jacketed blender was cooled to 25° C. in 80 min. The product was neutralized by addition of 83 g sodium bicarbonate and 60 min mixing at 25° C. and 6 full rotations per minute.

Comparative Example A

Step D)

For comparative purposes the HPMC, which had been used as a starting material for steps A) to C) of Examples 1-5, was partially depolymerized as described for Examples 1-5, step D) above, with the exception that the HPMC in Comparative Example A had not been subjected to steps A)-C) before carrying out the partial depolymerization step D).

As the HPMC, which had been used as a starting material for steps A) to C) of Examples 1-5 only had a moisture content of 1%, the HPMC was moistened with water prior to the partial depolymerization step to 6.0% to adapt the moisture content used in the starting material in Comparative Example A to those in Examples 1-5.

The conditions and results of the partial depolymerization process are listed in Table 2 below.

TABLE 2

| (Comparative) Example | A | 1 | 2 | 3 | 4 | 5 |
|---|---|---|---|---|---|---|
| HPMC Moisture [%] | 6.0 | 6.8 | 6.8 | 4.0 | 6.1 | 5.4 |
| time for partial depolymerization [min.] | 55 | 65 | 65 | 55 | 60 | 65 |
| Resulting viscosity as 2 wt. aq. solution [mPa · s] | 5.2 | 4.8 | 4.3 | 4.7 | 5.3 | 4.5 |

Comparative Example B

As in Co-Pending Patent Application PCT/US12/031112

Steps A) to C) were carried out with a HPMC that had 28.4% methoxyl groups, 6% hydroxypropoxyl groups and a viscosity of 4.3 mPas, measured as a 2.0% by weight solution in water at 20° C. The HPMC used as a starting material is commercially available from The Dow Chemical Company as Methocel™ F4 hydroxypropyl methylcellulose. Such materials are obtained by partial depolymerization of a HPMC of higher viscosity using dry hydrogen chloride gas, as in step D) of the process of the present invention.

The operating procedure in steps A)-C) was run in such a manner to obtain a cold water dispersible particulate HPMC having an untapped and tapped bulk density within the ranges obtained in Examples 1-5 for comparative purposes. While grinding and partial drying process step B) could be efficiently run with a HPMC of 73-75% moisture before grinding, the HPMC of Comparative Example B could be efficiently run at 43% in view of the lower HPMC viscosity.

Accordingly, Comparative Example B represents a procedure wherein the process steps A)-C) are preceded by the partial depolymerization step D) instead of carrying out process steps A)-D) in sequence as in the process of the present invention.

Comparative Material C)

The tapped and untapped bulk density (BD), the viscosity and the APHA color units of the commercially available Methocel™ F4 hydroxypropyl methylcellulose, which was used as a starting material in Comparative Example B, were measured and listed in Table 3 below, together with the same properties of Examples 1-5 and Comparative Examples A and B.

TABLE 3

| (Comparative) Example | BD untapped [g/l] | BD tapped [g/l] | Carr Index | Viscosity (2% aq. sol.) [mPa·s] | Color (2% aq. sol) APHA | Cold Water Dispersible (yes/no) |
|---|---|---|---|---|---|---|
| 1 | 435 | 508 | 14 | 4.8 | 34 | Yes |
| 2 | 436 | 513 | 15 | 4.3 | 33 | Yes |
| 3 | 505 | 599 | 16 | 4.7 | 35 | Yes |
| 4 | 509 | 594 | 14 | 5.3 | 35 | Yes |
| 5 | 456 | 536 | 15 | 4.5 | 31 | Yes |
| A | 294 | 438 | 33 | 5.2 | 34 | No |
| B | 493 | 552 | 11 | 4.4 | 44 | Yes |
| C | 345 | 475 | 27 | 4.3 | 34 | No |

In Examples 1-5 and in Comparative Example A the untapped and tapped bulk densities (BD) and the Carr Index were measured before partial depolymerization of the solid particles with gaseous HCl. The partial depolymerization does not significantly influence the untapped and tapped BD and the Carr Index.

The comparison between Examples 1-5 and Comparative Example B illustrates that surprisingly a cold water dispersible cellulose derivative of lower solution color is obtained if a partial depolymerization step (step D)) is conducted after a drying-grinding operation (steps A)-C)) as in Examples 1-5 than if a partial depolymerization step precedes a drying-grinding operation.

What is claimed is:

1. A method of improving the flowability and/or the cold water dispersibility of a particulate cellulose derivative comprising the steps of
   A) providing a moist cellulose derivative having a moisture content of from 25 to 95 percent, based on the total weight of the moist cellulose derivative, with the proviso that no substantial amount of surface-treatment additive is added to the cellulose derivative,
   B) grinding and partially drying the moist cellulose derivative in a gas-swept impact mill wherein a gas fed into the impact mill has a temperature of 100° C. or less;
   C) contacting the ground and partially dried cellulose derivative with an additional amount of a drying gas outside the gas-swept impact mill, wherein the additional amount of drying gas outside the gas-swept impact mill has a higher temperature than the gas fed into the impact mill; and
   D) subjecting the cellulose derivative to partial depolymerization after having contacted the cellulose derivative with the drying gas in step C)
   to produce the particulate cellulose derivative,
   wherein the produced particulate cellulose derivative has
   i) an untapped bulk density of at least 370 g/l,
   ii) a Carr Index of 16 or less;
   iii) a viscosity of from 1.2 to 200 mPa·s, measured as a 2 weight-% solution in water at 20° C. according to DIN 51562-1:1999-01; and
   iv) a color of not more than 35 American Public Health Association (APHA) color units, determined as a 2 weight-% solution in water at 20° C. according to ASTM D1209-05(2011).

2. A particulate cellulose derivative having
   i) an untapped bulk density of at least 370 g/l,
   ii) a Carr Index of 16 or less;
   iii) a viscosity of from 1.2 to 200 mPa·s, measured as a 2 weight-% solution in water at 20° C. according to DIN 51562-1:1999-01; and
   iv) a color of not more than 35 American Public Health Association (APHA) color units, determined as a 2 weight-% solution in water at 20° C. according to ASTM D1209-05(2011).

3. The particulate cellulose derivative of claim 2 having a median Equivalent Projected Circle Diameter (EQPC) of at least 50 micrometers.

4. An aqueous composition produced by blending water, the particulate cellulose derivative of claim 2 and one or more optional additives.

5. A process for the manufacture of capsules comprising the step of contacting the aqueous composition of claim 4 with dipping pins.

6. A process for coating a dosage form comprising the step of contacting the aqueous composition of claim 4 with the dosage form.

7. The particulate cellulose derivative of claim 2 being one of an alkyl cellulose, hydroxyalkyl cellulose or hydroxyalkyl alkylcellulose.

8. The particulate cellulose derivative of claim 2 being hydroxypropyl methylcellulose.

9. The particulate cellulose derivative of claim 2 having an untapped bulk density of at least 430 g/l.

10. The particulate cellulose derivative of claim 2 having a median Length of Fiber (LEFI) of from 50 to 600 micrometers.

11. The particulate cellulose derivative of claim 2 having a median Length of Fiber (LEFI) of from 100 to 400 micrometers.

12. The particulate cellulose derivative of claim 2 having a median Equivalent Projected Circle Diameter (EQPC) of from 100 to 300 micrometers.

\* \* \* \* \*